United States Patent
George et al.

(10) Patent No.: US 10,239,804 B2
(45) Date of Patent: Mar. 26, 2019

(54) PROCESS FOR THE PREPARATION OF 2,3,3,3-TETRAFLUOROPROPENE FROM METHYL CHLORIDE AND CHLORODIFLUOROMETHANE

(71) Applicant: SRF LIMITED, Gurgaon (IN)

(72) Inventors: Jose George, Gurgaon (IN); Rajasekaran Ramanathan, Gurgaon (IN); Sunil Raj, Gurgaon (IN); Anurag Katiyar, Gurgaon (IN); Ambuj Mishra, Gurgaon (IN); Rajdeep Anand, Gurgaon (IN)

(73) Assignee: SRF LIMITED, Gurgaon (IN)

( * ) Notice: Subject to any disclaimer, the term of this patent is extended or adjusted under 35 U.S.C. 154(b) by 0 days.

(21) Appl. No.: 15/756,320

(22) PCT Filed: Jan. 5, 2017

(86) PCT No.: PCT/IN2017/050006
§ 371 (c)(1),
(2) Date: Feb. 28, 2018

(87) PCT Pub. No.: WO2017/122222
PCT Pub. Date: Jul. 20, 2017

(65) Prior Publication Data
US 2018/0251416 A1 Sep. 6, 2018

(30) Foreign Application Priority Data

| Jan. 14, 2016 | (IN) | 201611001482 |
| Jan. 21, 2016 | (IN) | 201611002348 |
| Feb. 26, 2016 | (IN) | 201611006809 |
| Apr. 1, 2016 | (IN) | 201611011700 |
| Jun. 9, 2016 | (IN) | 201611019870 |

(51) Int. Cl.
*C07C 17/278* (2006.01)
*C07C 17/269* (2006.01)
*C07C 17/383* (2006.01)
*C07C 21/18* (2006.01)
*C07C 17/389* (2006.01)

(52) U.S. Cl.
CPC .......... *C07C 17/278* (2013.01); *C07C 17/269* (2013.01); *C07C 17/383* (2013.01); *C07C 17/389* (2013.01); *C07C 21/18* (2013.01)

(58) Field of Classification Search
None
See application file for complete search history.

(56) References Cited

U.S. PATENT DOCUMENTS

| 2,931,840 | A | 4/1960 | Marquis |
| 8,252,964 | B2 | 8/2012 | Devic et al. |
| 9,206,096 | B2 | 12/2015 | Furuta et al. |
| 2010/0162738 | A1 | 7/2010 | Low et al. |
| 2015/0291490 | A1* | 10/2015 | Furuta .................. C07C 17/386 570/178 |

FOREIGN PATENT DOCUMENTS

| EP | 2826766 | 1/2015 |
| JP | S40-2132 | 2/1965 |
| WO | WO-2013151070 A1 * | 10/2013 ........... C07C 17/269 |
| WO | WO 2015/053339 | 4/2015 |

OTHER PUBLICATIONS

WO2013151070A1, Oct. 10, 2013, pp. 1-13; English translation (Year: 2013).*
UOP (An introduction to Zeolite Molecular sieves, pp. 1-20).*
International Search Report and Written Opinion issued in International Patent Application No. PCT/IN2017/050006, dated May 12, 2017.

* cited by examiner

*Primary Examiner* — Medhanit W Bahta
(74) *Attorney, Agent, or Firm* — Norton Rose Fulbright US LLP

(57) ABSTRACT

The present invention relates to a process for preparation of olefins containing fluorine.

7 Claims, No Drawings

PROCESS FOR THE PREPARATION OF 2,3,3,3-TETRAFLUOROPROPENE FROM METHYL CHLORIDE AND CHLORODIFLUOROMETHANE

CROSS-REFERENCE TO RELATED APPLICATIONS

This application is a national phase application under 35 U.S.C. § 371 of International Application No. PCT/IN2017/050006 filed 5 Jan. 2017, which claims priority to Indian Application No. 201611001482 filed 14 Jan. 2016, Indian Application No. 201611002348 filed 21 Jan. 2016, Indian Application No. 201611006809 filed 26 Feb. 2016, Indian Application No. 201611011700 filed 1 Apr. 2016, and Indian Application No. 201611019870 filed 9 Jun. 2016. The entire contents of each of the above-referenced disclosures is specifically incorporated herein by reference without disclaimer.

FIELD OF THE INVENTION

The present invention relates to a process for preparation of olefins containing fluorine.

BACKGROUND OF THE INVENTION

Olefins containing fluorine compounds play an important role as refrigerant. In recent years, one of olefin containing compound namely 2,3,3,3-tetrafluoropropene (HFO-1234yf) has attracted attention as a new refrigerant to replace another fluorinated refrigerant namely 1,1,1,2-tetrafluoroethane (HFC-134a) which is a greenhouse gas.

The JP Application No. 40-2132 describes a process for the preparation of olefins containing fluorine by heating a mixture of methyl chloride and chlorodifluoromethane in the mol ratio of 5:1 at the temperature range of 600° C. to 1000° C. in the presence of steam.

The U.S. Pat. No. 2,931,840 describes a process for the preparation of HFO-1234yf by heating and decomposing a mixture of methyl chloride and chlorodifluoromethane or tetrafluoroethylene at a temperature of from 700 to 950° C. by a common heating means such as an electric heater in a reactor.

The U.S. Pat. No. 9,206,096 describes a process for the production of 2,3,3,3-tetrafluoropropene (HFO-1234yf) from chlorodifluoromethane (R22) and methyl chloride (R40), such amounts that the R40 would be in a ratio of from 0.01 to 3 mol to 1 mol of the R22. One of the byproduct formed in the reaction is chloro trifluoroethylene (CTFE). The boiling point of CTFE is −28° C. which is very close to the boiling point (−29° C.) of 2,3,3,3-tetrafluoropropene and thus, it becomes a challenge to separate or purify 2,3,3,3-tetrafluoropropene by routine separation and/or purification techniques, such as distillation.

In the present invention, by using a higher molar ratio, we have found that CTFE formed in comparison to 2,3,3,3-tetrafluoropropene can be substantially reduced and it is possible to obtain 2,3,3,3-tetrafluoropropene having a higher purity.

U.S. Pat. No. 8,252,964 describes a process for purification of 2,3,3,3-tetrafluoropropene containing saturated halogenated impurities using molecular sieves of size 5 Å to 11 Å. The saturated halogenated impurities mentioned are 236ea, 245eb, R254. Such impurities are bulky in nature and therefore requires molecular sieves of size greater than 7.5 Å.

U.S. application Ser. No. 12/308,327 describes a process of drying a fluid comprising a 2,3,3,3-tetrafluoropropene and water using molecular sieve of size 3 Å to 5 Å. PCT Publication No. 2015/053339 describes a process for purification of 2,3,3,3-tetrafluoropropene by distillation of composition 2,3,3,3-tetrafluoropropene and the methyl chloride and the fluorinated compounds having a boiling point of −14 to −30° C. Such composition upon distillation forms azeotropic composition and the azeotrope like composition of 2,3,3,3-tetrafluoropropene and the methyl chloride. U.S Patent Application No. 2015/0291490 describes a process for separation of 2,3,3,3-tetrafluoropropene and methyl chloride from azeotrope or azeotrope-like composition of 2,3,3,3-tetrafluoropropene and methyl chloride by contacting such composition with specific extraction solvent. An azeotrope composition of 2,3,3,3-tetrafluoropropene and methyl chloride is defined as a composition wherein the content ratio of 2,3,3,3-tetrafluoropropene and methyl chloride is mol % ratio of 63 mol % and 37 mol % respectively. An azeotrope-like composition is a composition wherein the content ratio of 2,3,3,3-tetrafluoropropene is 58 to 78 mol % and content ratio of methyl chloride is 22 to 42 mol %.

In view of the above, there is an urgent need to develop an industrially advantageous, efficient process for preparing 2,3,3,3-tetrafluoropropene.

The present inventors have surprisingly observed upon treatment of an anhydrous mixture comprising 2,3,3,3-tetrafluoropropene and methyl chloride, with molecular sieves of size 3 Å to 5 Å resulted in the selective adsorption of methyl chloride. Thus, aiding in the purification of 2,3,3,3-tetrafluoropropene. It has also been observed that the process of 2,3,3,3-tetrafluoropropene become industrially viable when methyl chloride and chlorodifluoromethane has been taken in molar ratio 3.2 to 4.7.

OBJECT OF THE INVENTION

The main objective of the present invention is to provide a process for preparation of olefins containing fluorine namely 2,3,3,3-tetrafluoropropene.

SUMMARY OF THE INVENTION

The first aspect of present invention discloses a process for preparation of 2,3,3,3-tetrafluoropropene comprising;
  a) providing a mixture of methyl chloride to chlorodifluoromethane, in a molar ratio of 3.2 to 4.7 in a reactor,
  b) providing and contacting heat medium with step a) mixture to form second mixture comprising 2,3,3,3-tetrafluoropropene, methyl chloride and fluorinated compounds,
  c) drying the second mixture of step b) to obtain anhydrous second mixture,
  d) contacting the anhydrous second mixture of step c) with molecular sieve of size 3 Å to 5 Å to obtain a mixture free of methyl chloride, and
  e) isolating 2,3,3,3-tetrafluoropropene from step d).

The second aspect of the present invention discloses a process for the preparation of 2,3,3,3-tetrafluoropropene comprising;
  a) providing a mixture of methyl chloride and chlorodifluoromethane in first reactor, wherein said mixture is either premixed or added separately,
  b) providing and contacting heat medium with step a) mixture to form second mixture comprising 2,3,3,3-tetrafluoropropene, methyl chloride and the fluorinated compounds having a boiling point of −14 to −90° C., c) drying the second mixture of step b) to obtain anhydrous second mixture,
d) subjecting the anhydrous second mixture of step c) to distillation to obtain anhydrous third mixture mainly comprises of methane, trifluoromethane, chlorotrifluoroethene, chlorodifluoromethane, tetrafluoroethyelene, vinylidene fluoride and difluoromethane and anhydrous fourth mixture mainly comprises of 2,3,3,3-tetrafluoropropene, methyl chloride, octafluorocyclobutane, chlorotrifluoroethyelene and tetrafluorochloroethane,
e) contacting the anhydrous third mixture of step d) with molecular sieve of size 3 Å to 5 Å to obtain a fifth mixture, said mixture is free of difluoromethane, optionally recycling the fifth mixture into the second reactor
f) subjecting the anhydrous fourth mixture of step d) to distillation to obtain anhydrous sixth mixture comprises of 2,3,3,3-tetrafluoropropene and methyl chloride,
g) optionally, purifying the anhydrous sixth mixture by contacting the step f) anhydrous sixth mixture with solvent in a solvent scrubber,
h) contacting the anhydrous sixth mixture of step f) or step g) or both with molecular sieve of size 3 Å to 5 Å to obtain seventh mixture, said mixture is free of methyl chloride,
i) isolating 2,3,3,3-tetrafluoropropene from the seventh mixture of step h).

The third aspect of the present invention discloses a process for regeneration of molecular sieves and recovery of the material adsorbed, comprising;
a) process to prepare the composition for regeneration of molecular sieves of size 3 Å to 5 Å, which includes the difluoromethane or methyl chloride or both,
b) heating the molecular sieves bed to 100° C. to 300° C. to desorb difluoromethane and methyl chloride,
c) contacting steam or difluoromethyl chloride or methyl chloride or nitrogen or difluoromethane or any other organic compound, formed in reaction between difluoromethyl chloride and methyl chloride, with heated molecular seive bed of step b) in order to regenerate molecular seives and to recover adsorbed material as a mixture comprising difluoromethane and contacted steam or methyl chloride and contacted steam or both and contacted steam; and
d) isolating difluoromethane or methyl chloride or both from the mixture of step c).

The fourth aspect of the present invention discloses a process for the preparation of 2,3,3,3-tetrafluoropropene comprising;
a) a process to prepare non-azeotropic composition which comprises 2,3,3,3-tetra fluoro propene and the methyl chloride,
b) process to supply the step a) non-azeotropic composition for solvent scrubbing by contacting the step a) non-azeotropic composition with solvent in a solvent scrubber to separate the step a) non-azeotropic composition into a first fraction in which content ratio of methyl chloride in the total amount of 2,3,3,3-tetrafluoropropene and the methyl chloride is lower than the content ratio of methyl chloride in total amount of the step a) non-azeotropic composition, and a second fraction in which the content ratio of methyl chloride in the total amount of 2,3,3,3-tetrafluoropropene and the methyl chloride is higher than the content ratio of methyl chloride in the step a) non-azeotropic composition, and c) obtaining 2,3,3,3-tetrafluoropropene from the first fraction.

The fifth aspect of the present invention discloses a process for the preparation of 2,3,3,3-tetrafluoropropene comprising;
a) providing a mixture of methyl chloride to chlorodifluoromethane in first reactor, wherein said mixture is either premixed or mixed separately,
b) providing and contacting the heat medium with step a) mixture to form second mixture comprises 2,3,3,3-tetrafluoropropene, methyl chloride and the fluorinated compounds having a boiling point of −14 to −90° C.,
c) drying second mixture of step b) to obtain anhydrous second mixture,
d) subjecting anhydrous second mixture of step c) to distillation to obtain anhydrous third mixture comprises methane, trifluoromethane, chlorotrifluoroethene, chlorodifluoromethane, tetrafluoroethyelene, vinylidene fluoride and difluoromethane and anhydrous fourth mixture mainly comprising of 2,3,3,3-tetrafluoropropene, methyl chloride, octafluorocyclobutane, chlorotrifluoroethyelene and tetrafluorochloroethane,
e) contacting anhydrous third mixture of step d) with molecular sieve of size 3 Å to 5 Å to obtain a fifth mixture, said mixture is free of difluoromethane,
f) providing the fifth mixture and steam into a second reactor to obtain a second mixture free of methyl chloride,
g) drying the second mixture free of methyl chloride to obtain anhydrous second mixture, alone or in combination with step c),
h) subjecting the anhydrous second mixture of step g) to distillation to obtain anhydrous third mixture mainly comprising of methane, tetrafluoroethyelene, vinylidene fluoride and difluoromethane and anhydrous fourth mixture mainly comprises of 2,3,3,3-tetrafluoropropene, methyl chloride, octafluorocyclobutane, chlorotrifluoroethyelene and tetrafluorochloroethane, as separately or in combination with step d),
i) subjecting the anhydrous fourth mixture of step d) and/or step h) to distillation to obtain anhydrous sixth mixture mainly comprises of 2,3,3,3-tetrafluoropropene and methyl chloride, and another mixture mainly comprises of methyl chloride, octafluorocyclobutane, chlorotetrafluoroethane and tetrafluoroethane,
j) contacting anhydrous sixth mixture of step i) with molecular sieve of size 3 Å to 5 Å to obtain seventh mixture, said mixture is free of methyl chloride, and
k) isolating 2,3,3,3-tetrafluoropropene from seventh mixture of step j).

The sixth aspect of the present invention discloses a process for the preparation of 2,3,3,3-tetrafluoropropene comprising;
a) providing a mixture of methyl chloride to chlorodifluoromethane in a first reactor, said mixture is either p premixed or mixed separately,
b) providing and contacting the heat medium with step a) mixture to form a second mixture comprising 2,3,3,3-tetrafluoropropene, methyl chloride and the fluorinated compounds having a boiling point of −14 to −90° C.,
c) drying the second mixture of step b) to obtain an anhydrous second mixture,
d) contacting the anhydrous second mixture of step c) with a solvent to obtain an anhydrous mixture 3' in gas phase and anhydrous mixture 4' in liquid phase, wherein the anhydrous mixture 3' comprises of methane, tetrafluoroethyelene, trifluoromethane, vinylidene fluoride, difluoromethane, chlorotrifluoroethene, hexafluoropropene, chlorodifluoromethane, 2,3,3,3-tetrafluoropropene, octafluorocyclobutane and methyl chloride and anhydrous mixture 4' mainly comprises of solvent and methyl chloride, e) contacting the anhydrous mixture 3' with 4 Å molecular sieves to obtain a mixture 5' and a mixture 6', wherein the mixture 5' is free of methyl chloride and difluoromethane and the mixture 6' comprises of mainly methyl chloride and difluoromethane, f) subjecting the anhydrous mixture 4' of step d) to distillation to obtain a mixture 7' mainly comprises methyl chloride which is recycled into the existing reactor and an mixture 8' mainly comprises solvent which is reused, g) subjecting the mixture 5' of step e) to distillation to obtain a mixture 9' mainly comprises methane, tetrafluoroethyelene, trifluoromethane, vinylidene fluoride, hexafluoropropene and chlorodifluoromethane and a mixture 10' mainly comprises of chlorotrifluoroethyelene, 2,3,3,3-tetrafluoropropene, octafluorocyclobutane, tetrafluorochloroethane, tetrafluoroethane, h) recycling mixture 9' of step g) to the existing reactor or to the second reactor, i) subjecting the mixture 10' of step g) to distillation column to obtain an mixture 11' mainly comprises 2,3,3,3-tetrafluoropropene and chlorotrifluoroethyelene and a mixture 12' mainly comprises octafluorocyclobutane, chlorotetrafluoroethanes, tetrafluoroethane and heavies, j) subjecting the mixture 12' of step i) to distillation to obtain a mixture 13' mainly comprises octafluorocyclobutane, chlorotetrafluoroethanes, tetrafluoroethanes which is recycled into reactor, and k) isolating 2,3,3,3-tetrafluoropropene from the mixture 11'.

Another aspect of the present invention discloses that the heating of the reactor at a temperature in range of 550° C. to 900° C. or providing a steam medium to mixture of methyl chloride and chlorodifluoromethane to obtain a temperature range of 550° C. to 900° C. or both, to obtain a second mixture.

Another aspect of the present invention discloses that an anhydrous second mixture is obtained by passing the second mixture through water quencher, caustic scrubber, sulphuric scrubber, alumina balls or calcium chloride.

Another aspect of the present invention discloses that the solvent used for scrubbing is selected from the group consisting of chloroform, dichloromethane, trichloroethylene, methanol or mixture thereof.

DETAILED DESCRIPTION OF THE INVENTION

The present invention discloses a process for the preparation of olefins containing fluorine. In this process there is formation of non azeotropic mixtures.

In present invention a non azeotropic mixture stands for the composition attained when the top temperature (reflux temperature) is maintained in between the boiling point of two components which has to be separated. In present invention the boiling point of methyl chloride is −24.2° C. and boiling point of 2,3,3,3-tetrafluoropropene is −30° C. If the top temperature (reflux temperature) is maintained in between −24.2° C. and −30° C. then the top composition achieved is called non azeotropic mixture.

The first aspect of the present invention discloses a process for the preparation of 2,3,3,3-tetrafluoropropene comprises a mixture of methyl chloride to chlorodifluoromethane, in a molar ratio of 3.2 to 4.7, is provided in a reactor. The methyl chloride and chlorodifluoromethane may be preliminarily mixed and provided in a reactor or methyl chloride and chlorodifluoromethane may be separately added into the reactor to form a mixture. The resulting mixture is provided or contacted with the heat medium to form second mixture comprising 2,3,3,3-tetrafluoropropene and methyl chloride.

The heat medium is refer to reactor heated to the temperature range of 550° C. to 900° C. or providing a steam medium, to the mixture of methyl chloride to chlorodifluoromethane to obtain the temperature range of 550° C. to 900° C. in the reactor, or both to obtain second mixture. Then the second mixture is dried to obtain anhydrous second mixture.

The drying can be done by treating second mixture with drying agent. The drying agent may be selected from water quencher, caustic scrubber, sulphuric scrubber, alumina balls or calcium chloride.

The anhydrous second mixture comprising 2,3,3,3-tetrafluoropropene and methyl chloride is contacted with molecular sieve of size 3 Å to 5 Å to obtain a mixture free of methyl chloride. Then, 2,3,3,3-tetrafluoropropene is isolated from resulting reaction mixture.

The isolation of 2,3,3,3-tetrafluoropropene can be carried out by any method known in the art, for example, by series of distillations.

In second aspect of the present invention discloses a process for the preparation of 2,3,3,3-tetrafluoropropene comprises a mixture of methyl chloride (R40) to chlorodifluoromethane (R22) is provided in a reactor. The mixture of methyl chloride (R40) and chlorodifluoromethane (R22) would be in a molar ratio of 3.2 to 4.7. The methyl chloride and chlorodifluoromethane may be preliminarily mixed and provided in a reactor or methyl chloride and chlorodifluoromethane may be separately added into the reactor to form a mixture. The resulting mixture is provided or contacted with the heat medium to form second mixture comprising 2,3,3,3-tetrafluoropropene, methyl chloride and the fluorinated compounds having a boiling point of −14 to −90° C. The heat medium is refer to reactor heated to the temperature range of 550° C. to 900° C. or providing a steam medium, to the mixture of methyl chloride to chlorodifluoromethane to obtain the temperature range of 550° C. to 900° C. in the reactor, or both to obtain second mixture. Then the second mixture is dried to obtain anhydrous second mixture. The anhydrous second mixture may be obtained by treating second mixture with drying agent. The drying agent may be selected from water quencher, caustic scrubber, sulphuric scrubber, alumina balls or calcium chloride.

The anhydrous second mixture thus obtained is subjected to distillation to obtain anhydrous third mixture mainly comprising of methane, trifluoromethane, chlorotrifluoroethene, chlorodifluoromethane, tetrafluoroethyelene, vinylidene fluoride and difluoromethane and anhydrous fourth mixture mainly comprising of 2,3,3,3-tetrafluoropropene, methyl chloride, octafluorocyclobutane, chlorotrifluoroethyelene and tetrafluorochloroethane, Then, anhydrous third mixture is contacted with molecular sieve of size 3 Å to 5 Å to obtain a fifth mixture, which is free of difluoromethane and can be recycled back into the reactor.

The anhydrous fourth mixture is subjected to distillation to obtain anhydrous sixth mixture comprising 2,3,3,3-tetrafluoropropene and methyl chloride. Optionally, anhydrous sixth mixture can be purified by contacting anhydrous sixth mixture with solvent in a solvent scrubber.

The sixth mixture resulting from with or without purification is contacted with molecular sieve of size 3 Å to 5 Å to obtain seventh mixture, which is free of methyl chloride.

Optionally, regeneration of molecular sieves, recovery of the material adsorbed can be done by heating the molecular sieves bed at a temperature 100° C. to 300° C. to obtain adsorbed material comprising difluoromethane and methyl chloride; contacting steam or difluoromethyl chloride or difluoromethane or methyl chloride, or nitrogen or any other organic compounds formed in the reaction during regeneration process through adsorbed material to obtain a mixture.

Finally, 2,3,3,3-tetrafluoropropene is isolated from seventh mixture. The isolation of 2,3,3,3-tetrafluoropropene from seventh mixture is carried out by any method known in the art, for example, distillation, adsorption, absorption and mixture thereof.

In third aspect of the present invention discloses a process for regeneration of molecular sieves and recovery of the material adsorbed, comprising a process to prepare the composition, for regeneration of molecular sieves of size 3 Å to 5 Å, which includes the difluoromethane or methyl chloride or both. The molecular sieves is heated at a temperature 100° C. to 300° C. to obtain adsorbed material comprising difluoromethane and methyl chloride. A steam or difluoromethyl chloride or difluoromethane or methyl chloride, or nitrogen or any other organic compounds formed in the reaction between difluoromethyl chloride and methyl chloride, is contacted with heated molecular seive bed in order to regenerate molecular seives to recover adsorbed material as a mixture comprising difluoromethane and contacting steam or methyl chloride and contacting steam or both and contacting steam. Difluoromethyl chloride and methyl chloride or both are isolated from reaction mixture.

In fourth aspect of the present invention discloses a process for the purification of 2,3,3,3-tetrafluoropropene comprising the process to prepare the non-azeotropic composition which includes mainly a 2,3,3,3-tetrafluoropropene and the methyl chloride. The non-azeotropic composition thus obtained is contacted with solvent in a solvent scrubber to separate non-azeotropic composition into a first fraction in which the content ratio of methyl chloride in the total amount of 2,3,3,3-tetrafluoropropene and the methyl chloride is lower than the content ratio of methyl chloride in total amount of the non-azeotropic composition, and a second fraction in which the content ratio of methyl chloride in the total amount of 2,3,3,3-tetrafluoropropene and the methyl chloride is higher than the content ratio of methyl chloride in the non-azeotropic composition and 2,3,3,3-tetrafluoropropene is isolated from the first fraction.

The solvent used in solvent scrubber consists of chlorinated hydrocarbon, fluorinated hydrochlorocarbon, alcohol, an ether, a nitrile, a ketone, a carbonate, an amine, an ester, dimethylformamide.

The 2,3,3,3-tetrafluoropropene is isolated from the first fraction by methods known in the art, for example, azeotropic distillation, extractive distillation, absorption and adsorption or mixture thereof.

In fifth aspect of the present invention discloses a process for the preparation of 2,3,3,3-tetrafluoropropene comprises a mixture of methyl chloride (R40) to chlorodifluoromethane (R22) is provided in a first reactor.

The mixture of methyl chloride (R40) to chlorodifluoromethane (R22) may be in molar ratio of 3.2 to 4.7. The methyl chloride and chlorodifluoromethane may be preliminarily mixed and provided in a reactor or methyl chloride and chlorodifluoromethane may be separately added into the reactor to form a mixture.

The heat medium is refer to reactor heated to the temperature range of 550° C. to 900° C. or providing a steam medium, to the mixture of methyl chloride to chlorodifluoromethane to obtain the temperature range of 550° C. to 900° C. in the reactor, or both to obtain second mixture.

The anhydrous second mixture is obtained by passing the second mixture through a drying agent such as water quencher, caustic scrubber, sulphuric scrubber and alumina balls or calcium chloride. The anhydrous second mixture is subjected to distillation, to obtain anhydrous third mixture mainly comprising of methane, trifluoromethane, chlorotrifluoroethene, tetrafluoroethyelene, vinylidenefluoride, trifluoromethane and difluoromethane and anhydrous fourth mixture mainly comprising of 2,3,3,3-tetrafluoropropene, methyl chloride, chlorotrifluoroethyelene, octafluorocyclobutane and tetrafluoroethane. The third mixture thus obtained is contacted with molecular sieve of size 3 Å to 5 Å in molecular sieves bed to obtain a fifth mixture, which is free of difluoromethane and can be recycled through second reactor.

The second reactor is operated at higher temperature than the first reactor. The reactor is heated by superheated steam or electrical heaters or combination of both.

The fifth mixture can be recycled by providing fifth mixture and steam into a second reactor to obtain a second mixture. The second mixture is dried as separately or in combination with earlier obtained second mixture to give anhydrous second mixture. The anhydrous second mixture is subjected to distillation to obtain anhydrous third mixture mainly comprising of methane, tetrafluoroethyelene, vinylidene fluoride and difluoromethane and anhydrous fourth mixture mainly comprising of 2,3,3,3-tetrafluoropropene, methyl chloride, octafluorocyclobutane, chlorotrifluoroethyelene and tetrafluorochloroethane.

The resulting anhydrous fourth mixture thus obtained and/or earlier obtained anhydrous fourth mixture is subjected to another distillation to obtain anhydrous sixth mixture mainly comprising of 2,3,3,3-tetrafluoropropene and methyl chloride and another mixture comprising mainly of octafluorocyclobutane, tetrafluorochloroethane, tetrafluoroethane. Such distillation does not involve the formation of azeotrope and azeotrope like compositions of 2,3,3,3-tetrafluoropropene and the methyl chloride.

The another mixture thus obtained can be subjected to another distillation, to obtain eighth mixture and ninth mixture. The eighth mixture comprising mainly of octafluorocyclobutane, tetrafluorochloroethane, tetrafluoroethane which is recycled back into first reactor and ninth mixture which constitutes heavies is sent for incineration.

The anhydrous sixth mixture mainly comprising 2,3,3,3-tetrafluoropropene and methyl chloride is contacted with molecular sieve of size 3 Å to 5 Å to obtain seventh mixture, which is free of methyl chloride. The isolation of 2,3,3,3-tetrafluoropropene from seventh mixture is carried out by any method known in the art, for example, distillation, adsorption, absorption and mixture thereof.

The sixth aspect of the present invention discloses a process for the preparation of 2,3,3,3-tetrafluoropropene comprises, a mixture of methyl chloride (R40) to chlorodifluoromethane (R22) is provided in a first reactor. The mixture methyl chloride (R40) to chlorodifluoromethane (R22) would be in a molar ratio of 3.2 to 4.7. The methyl chloride and chlorodifluoromethane may be preliminarily mixed and provided in a reactor or methyl chloride and chlorodifluoromethane may be separately added into the reactor to form a mixture.

The heat medium refer to reactor heated to the temperature range of 550° C. to 900° C. or providing a steam medium, to the mixture of methyl chloride to chlorodifluoromethane to obtain the temperature range of 550° C. to 900° C. in the reactor, or both to obtain the second mixture.

The anhydrous second mixture may be obtained by treating second mixture with drying agent to obtain anhydrous second mixture.

The anhydrous second mixture is contacted with a solvent to obtain an anhydrous mixture 3' in gas phase and anhydrous mixture 4' in liquid phase, wherein the anhydrous mixture 3' comprises of methane, tetrafluoroethyelene, trifluoromethane, vinylidene fluoride, difluoromethane, chlorotrifluoroethene, hexafluoropropene, chlorodifluoromethane, 2,3,3,3-tetrafluoropropene, octafluorocyclobutane and methyl chloride and anhydrous mixture 4' mainly comprises of solvent and methyl chloride.

The anhydrous mixture 3' is contacted with 3 Å to 5 Å molecular sieves to obtain a mixture 5' and a mixture 6'. The mixture 5' is free of methyl chloride, difluoromethane and the mixture 6' comprises of mainly methyl chloride and difluoromethane.

The anhydrous mixture 4' is subjected to distillation to obtain a mixture 7' mainly comprising of methyl chloride which is recycled back into the existing reactor and an mixture 8' mainly comprising of solvent which can be reused back.

The mixture 5' is subjected to distillation to obtain a mixture 9' mainly comprising of methane, tetrafluoroethyelene, trifluoromethane, vinylidene fluoride, hexafluoropropene and chlorodifluoromethane and a mixture 10' mainly comprising of chlorotrifluoroethylene, 2,3,3,3-tetrafluoropropene, octafluorocyclobutane, tetrafluorochloroethane, tetrafluoroethane.

The mixture 9' is recycled to the existing reactor or to the second reactor and the mixture 10' is subjected to distillation column to obtain an mixture 11' mainly comprising of 2,3,3,3-tetrafluoropropene and chlorotrifluoroethyelene and a mixture 12' mainly comprising of octafluorocyclobutane, chlorotetrafluoroethanes, tetrafluoroethane and heavies. The mixture 12' is subjected to distillation to obtain a mixture 13' mainly comprising of octafluorocyclobutane, chlorotetrafluoroethanes, tetrafluoroethanes which will be recycled back into reactor. Finally, 2,3,3,3-tetrafluoropropene is isolated from the mixture 11'. Isolation of 2,3,3,3-tetrafluoropropene from the eleventh mixture may be carried by any method selected from distillation, extraction, adsorption, absorption and hydrogenation or mixture thereof.

While the present invention has been described in terms of its specific embodiments, certain modifications and equivalents will be apparent to those skilled in the art and are intended to be included within the scope of the present invention.

EXAMPLES

Example 1: Process for the Preparation of 2,3,3,3-tetrafluoropropene

Water (380 g/hour) was passed through steam jacketed preheater, where the temperature was raised to 160° C. followed by electrical super heater where the temperature of steam was raised to 800° C. This superheated steam goes to the reactor whose temperature was maintained at 775° C. either by superheated steam or by electrical heaters. After adjusting the water flow rate, R-22 and R-40 were passed through their respective preheaters at the rate of 105 g/hour and 250 g/hour respectively and then mixed in organic super heater where the temperature was maintained at 600° C. followed by reactor which was maintained at 775° C. The residence time in the reaction system was maintained at around 0.5 seconds.

The analysis of Reactor outlet was given below after eliminating water and acids. The reactor outlet stream was recycled back into the reactor and reaction was made continuous in nature.

| Methane | 0.52% | R-22 | 1.43% |
| TFE | 4.42% | R-1234yf | 3.20% |
| VdF | 6.88% | OFCB | 0.08% |
| Trifluoroethene | 0.04% | C-1 | 81.65% |
| CTFE | 0.08% | R-134 | 0.34% |
| HFP | 0.12% | R-124a | 0.01% |
| | | R-124 | 0.04% |

Purification:

The reactor outlet stream was then passed through a quencher, where the temperature of the reaction mass was cooled below 100° C. and then it was passed through a serious of caustic scrubber and sulfuric acid scrubber followed by alumina ball dryer to remove acidity and moisture. The 2.4 kg of 4 Å molecular sieves was taken and the reactor outlet stream was passed through this molecular sieves bed, to give following results:

| | | Molecular Sieves used 4 A° | | | | |
| --- | --- | --- | --- | --- | --- | --- |
| Compounds | Before Adsorber | After Adsorber 14 min | After Adsorber 49 min | After Adsorber 79 min | After Adsorber 129 min | After Adsorber 189 min |
| Methane | 1.2357% | 6.33% | 1.18% | 0.97% | 0.84% | 0.77% |
| TFE | 32.5231% | 93.10% | 59.06% | 48.90% | 46.27% | 45.71% |
| R-23 | 4.0603% | 0.00% | 0.00% | 7.22% | 3.59% | 1.99% |
| VDF | 10.4500% | 0.00% | 35.40% | 15.34% | 13.18% | 13.01% |
| TriFEthene | 0.3832% | 0.00% | 0.00% | 1.60% | 0.54% | 0.38% |
| R-32 | 0.8648% | 0.00% | 0.00% | 0.00% | 0.00% | 0.00% |
| CTFE | 0.9042% | 0.00% | 0.53% | 1.35% | 0.97% | 0.94% |
| HFP + R12 | 1.1991% | 0.00% | 0.11% | 3.48% | 1.20% | 1.11% |
| R-22 | 10.9164% | 0.00% | 0.94% | 1.13% | 9.93% | 18.89% |
| R-1234yf | 8.0013% | 0.00% | 2.74% | 15.22% | 19.21% | 13.76% |
| OFCB | 0.5638% | 0.00% | 0.00% | 0.00% | 0.00% | 0.00% |
| R134a/R1122 | 0.8912% | 0.00% | 0.00% | 2.41% | 2.66% | 1.39% |
| C-1 | 23.2631% | 0.00% | 0.00% | 0.00% | 0.00% | 0.40% |

| Compounds | Before Adsorber | Molecular Sieves used 4 A° | | | | |
|---|---|---|---|---|---|---|
| | | After Adsorber 14 min | After Adsorber 49 min | After Adsorber 79 min | After Adsorber 129 min | After Adsorber 189 min |
| R-134 | 0.2431% | 0.00% | 0.00% | 0.04% | 0.00% | 0.03% |
| R124a | 0.4930% | 0.00% | 0.00% | 1.26% | 0.21% | 0.22% |
| R124 | 0.4884% | 0.00% | 0.00% | 0.28% | 0.04% | 0.11% |
| | 3.3554% | 0.57% | 0.04% | 0.81% | 1.03% | 1.02% |

Example 2: Process for the Preparation of 2,3,3,3-tetrafluoropropene

Water (380 gms/hour) is passed through steam jacketed preheater, where the temperature is raised to 160° C. followed by electrical super heater where the temperature of steam is raised to 800° C. This superheated steam goes to the reactor whose temperature is maintained at 775° C. either by superheated steam or by electrical heaters. After adjusting the water flow rate, R-22 and R-40 are passed through their respective preheaters at the rate of 105 gms/hour and 250 gms/hour respectively and then mixed in organic super heater where the temperature is maintained at 600° C. followed by reactor which is maintained at 775° C. The residence time in the reaction system is maintained at around 0.5 seconds.

The analysis of Reactor outlet is same as given in example 1 after eliminating water and acids. The reactor outlet stream was recycled back into the reactor and reaction was made continuous in nature.

Purification:

For checking the effect of 4 Å molecular sieves, experiment was conducted at 1:1 molar ratio of chlorodifluoromethane:methyl chloride at 750° C. with steam at a residence time of 0.5 seconds.

From the analysis data, it is clear that R-32 and methyl chloride (C-1) gets adsorbed on 4 Å molecular sieves. Based on these experimental details, the purification process is given below.

The reactor outlet stream passes through a quencher followed by caustic scrubber, sulphuric scrubber and then through alumina balls for making the organic mass anhydrous and acid free. This anhydrous organic mass is compressed and then transferred to distillation column 1, from where Methane, tetrafluoroethyelene, vinylidenefluoride, trifluoromethane, trifluoroethene, difluoromethane, hexafluoropropene and dichlorodifluoromethane is taken from the top. The top product from distillation column 1 is then passed to 4 Å molecular sieves to remove R-32 and the remaining material can be recycled back into reactor. The R-32 adsorbed in the molecular sieves can be recovered during regeneration step which is discussed later. The distillation column bottom which contains octafluorocyclobutane, chlorotrifluoroethyelene, 2,3,3,3-tetrafluoropropene, difluorochloroethyelene, methyl chloride, tetrafluoroethanes and tetrafluorochloroethane is sent to distillation column 2. In distillation column 2,2,3,3,3-tetrafluoropropene and methyl chloride in the mole ratio (55%:45% to 1%:99%) is recovered from the top and the rest of the material is recovered from the bottom and is transferred to third distillation column from where difluorochloroethyelene, methyl chloride, tetrafluoroethane, octafluorocyclobutane and tetrafluorochloroethane is taken from the top and the heavies collected at third distillation column bottom is sent to incineration. The top product from distillation column 2 consisting mainly of methyl chloride and 2,3,3,3-Tetrafluoropropene is passed through 4 Å molecular sieves where selective adsorption of methyl chloride takes place and methyl chloride free 2,3,3,3-tetrafluoropropene is obtained. The final purification of methyl chloride free 2,3,3,3-tetrafluoropropene can be done by distillation, absorption, adsorption and mixture thereof. The methyl chloride adsorbed can be recovered during regeneration step and recycled back into reactor.

Regeneration Step:

In the regeneration step, the bed temperature of the molecular sieves is raised to 120° C. and then steam is passed which aids the desorb material to come out of the bed (For Distillation column 1, difluoromethane and for distillation Column 2 methyl chloride). The temperature of the molecular sieves bed is slowly increased to 300° C. for complete desorption of difluoromethane and methyl chloride. The desorbed material along with steam is passed through distillation column from where difluoromethane and methyl chloride can be recovered. The recovered methyl chloride stream can be directly recycled to the reactor. After desorption, nitrogen is passed through the molecular sieves bed for making it dry and then it can be reused. The medium for carrying out desorb material can be steam, nitrogen, difluoromethyl chloride, methyl chloride, difluoromethane and any other organic compounds formed in the reaction.

Example 3: Process for the Preparation of 2,3,3,3-tetrafluoropropene

Water (403 gms/hour) is passed through steam jacketed SS preheater, where the temperature is raised to 160° C. followed by electrical inconel super heater where the temperature of steam is raised to 800° C. This superheated steam goes to the Inconel reactor whose temperature is maintained at 740° C. by superheated steam and electrical heaters. After adjusting the water flow rate, chlorodifluoromethane and methyl chloride are passed through their respective preheaters at the rate of 242 gms/hr and 141 gms/hr respectively and then mixed in organic super heater where the temperature is maintained at 400° C. followed by reactor where it mixes with steam. The residence time in the reactor is maintained at 0.5 seconds. The reactor outlet stream is made free of acids and moisture by quenching in water, followed by caustic wash, sulphuric wash and then passing the outlet stream through alumina balls. This anhydrous stream was then passed through solvent scrubber and the sample were analysed before and after the scrubber. The results are given below in G.C area %.

|  | Before Methanol Scrubber | After Methanol Scrubber Time of scrubbing | |
|---|---|---|---|
|  |  | 40 minutes | 90 minutes |
| Methane | 2.36% | 1.19% | 3.85% | 2.51% |
| TFE | 26.96% | 26.62% | 71.13% | 59.58% |
| R-23 | 0.34% | 0.32% | 0.51% | 0.56% |
| VdF | 3.05% | 2.969% | 6.33% | 5.98% |
| TriFEthene | 0.13% | 0.11% | 0.11% | 0.19% |
| R-32 | 0.49% | 0.45% | 0.38% | 0.49% |
| CTFE | 0.15% | 0.17% | 0.32% | 0.33% |
| HFP | 0.13% | 0.13% | 0.15% | 0.21% |
| R-22 | 10.33% | 9.80% | 2.67% | 5.04% |
| R-1234yf | 1.94% | 1.93% | 2.30% | 3.05% |
| OFCB | 0.26% | 0.20% | 0.06% | 0.20% |
| C-1 | 53.23% | 54.81% | 12.03% | 21.63% |
| R124a | 0.07% | 0.033% | 0% | 0% |
| R124 | 0.05% | 0.45% | 0% | 0% |

Example 4: Process for the Preparation of 2,3,3,3-tetrafluoropropene

The procedure followed is same as given in example 3, and the solvent has been changed to trichloroethylene. 4 kgs of trichloroethylene was taken for scrubbing. The analysis results before and after passing through trichloroethylene is given below.

|  | Before TCE Scrubber | After TCE Scrubber Time of Scrubbing | |
|---|---|---|---|
|  |  | 20 minutes | 40 minutes |
| Methane | 0.54% | 1.03% | 0.64% |
| TFE | 21.02% | 58.18% | 47.04% |
| R-23 | 0.18% | 0.26% | 0.42% |
| VdF | 1.65% | 7.14% | 6.26% |
| TriFEthene | 0.04% | 0.11% | 0.13% |
| R-32 | 0.16% | 0.26% | 0.33% |
| CTFE | 0.10% | 0.23% | 0.31% |
| HFP | 0.10% | 0.05% | 0.13% |
| R-22 | 27.70% | 10.47% | 14.83% |
| R-1234yf | 1.14% | 2.73% | 3.21% |
| OFCB | 0.10% | 0.19% | 0.18% |
| C-1 | 46.77% | 13.37% | 21.33% |
| R124a | 0.05% | 0.03% | 0.02% |
| R124 | 0.07% | 0% | 0.06% |

Example 5: Process for the Preparation of 2,3,3,3-tetrafluoropropene

The procedure followed is same as given in example 3, here the solvent has been changed to chloroform. 4 kgs of chloroform was taken for scrubbing. The analysis results before and after passing through chloroform is given below.

|  | Before TCE Scrubber | After TCE Scrubber Time of Scrubbing | |
|---|---|---|---|
|  |  | 23 minutes | 46 minutes |
| Methane | 0.19% | 0.60% | 0.15% |
| TFE | 23.94% | 48.36% | 56.77% |
| R-23 | 0.10% | 0.35% | 0.51% |
| VdF | 1.12% | 3.15% | 7.48% |
| TriFEthene | 0.03% | 0.06% | 0.11% |
| R-32 | 0.04% | 0.03% | 0.16% |
| CTFE | 0.09% | 0.14% | 0.43% |
| HFP | 0.04% | 0% | 0% |
| R-22 | 29.80% | 0.11% | 4.09% |
| R-1234yf | 0.89% | 0.37% | 2.12% |
| OFCB | 0.04% | 0% | 0.06% |
| C-1 | 42.08% | 0.15% | 3.40% |
| R124a | 0.03% | 0% | 0% |
| R124 | 0.03% | 0% | 0% |

Example 6: Process for the Preparation of 2,3,3,3-tetrafluoropropene

The procedure followed is same as given in example 3, only difference is reactor temperature was raised to 755° C. and the solvent has been changed to methylene chloride. 4 kgs of methylene chloride was taken for scrubbing. The analysis results before and after passing through methylene chloride is given below.

|  | Before TCE Scrubber | After TCE Scrubber (Time of Scrubbing) | |
|---|---|---|---|
|  |  | 15 minutes | 30 minutes |
| Methane | 0.16% | 0.37% | 0.14% |
| TFE | 22.32% | 40.70% | 21.25% |
| R-23 | 0.21% | 0.33% | 0.17% |
| VdF | 5.29% | 5.93% | 4.98% |
| TriFEthene | 0.07% | 0.01% | 0.06% |
| R-32 | 0.14% | 0% | 0.12% |
| CTFE | 0.24% | 0.23% | 0.22% |
| HFP | 0.21% | 0% | 0.20% |
| R-22 | 5.52% | 0.03% | 5.14% |
| R-1234yf | 3.62% | 0.48% | 3.52% |
| OFCB | 0.11% | 0% | 0.11% |
| C-1 | 61.35% | 0.19% | 34.38% |
| R124a | 0.02% | 0% | 0.02% |
| R124 | 0.10% | 0% | 0.08% |

From the analysis data, it is clear that methyl chloride (C-1) and R-22 gets preferentially absorbed in theses solvents. Based on this experimental details, the purification process is given below.

The reactor outlet stream passes through a quencher followed by caustic scrubber, sulphuric scrubber and then through alumina balls for making the organic mass anhydrous and acid free. This anhydrous organic mass is compressed and then transferred to distillation column 1, from where methane, tetrafluoroethyelene, vinylidenefluoride, trifluoromethane, trifluoroethene, difluoromethane, hexafluoropropene and dichlorodifluoromethane is taken from the top and can be recycled back. The distillation column bottom which contains octafluorocyclobutane, chlorotrifluoroethylene, 2,3,3,3-tetrafluoropropene, methyl chloride and tetrafluorochloroethane is sent to distillation column 2. In distillation column 2, the top fraction consists mainly of 2,3,3,3-tetrafluoropropene and methyl chloride in the mole ratio (55%:45% to 1%:99%) and the rest of the material is recovered from the bottom and is transferred to third distillation column from where methyl chloride, otafluorocyclobutane and tetrafluorochloroethane is taken from the top and recycled back into the reactor and the heavies collected at third distillation column bottom is sent to incineration.

The top product from distillation column 2 consisting mainly of methyl chloride and 2,3,3,3-Tetrafluoropropene is passed through solvent scrubber where selective absorption of methyl chloride takes place and 2,3,3,3-tetrafluoropropene containing less amount of methyl chloride is obtained which is passed through 4 Å molecular sieves to get mainly 2,3,3,3-tetrafluoropropene free of methyl chloride. The final purification of methyl chloride free 2,3,3,3-tetrafluoropropene can be done by azeotropic distillation, extractive distillation, absorption, adsorption and mixture thereof. The methyl chloride absorbed can be recovered from solvent through normal distillation.

The fraction coming out from the chloroform solvent scrubber was then passed through 4 Å molecular sieves bed to make 2,3,3,3-tetrafluoropropene free of methyl chloride.

| | Before C3 Scrubber | After C3 Scrubber Time of scrubbing | | After passing through 4 A° molecular sieves |
|---|---|---|---|---|
| | | 23 minutes | 46 minutes | |
| Methane | 0.19% | 0.60% | 0.45% | 0.26% |
| TFE | 23.94% | 48.36% | 56.77% | 78.54% |
| R-23 | 0.10% | 0.35% | 0.51% | 0% |
| VdF | 1.12% | 3.15% | 7.48% | 18.48% |
| TriFEthene | 0.03% | 0.06% | 0.11% | 0% |
| R-32 | 0.04% | 0.03% | 0.16% | 0% |
| CTFE | 0.09% | 0.14% | 0.43% | 0.10% |
| HFP | 0.04% | 0% | 0% | 0% |
| R-22 | 29.80% | 0.11% | 4.09% | 0.02% |
| R-1234yf | 0.89% | 0.37% | 2.12% | 2.45% |
| OFCB | 0.04% | 0% | 0.06% | 0% |
| C-1 | 42.08% | 0.15% | 3.40% | 0% |
| R124a | 0.03% | 0% | 0% | 0% |
| R124 | 0.03% | 0% | 0% | 0% |

Example 7: Process for the Preparation of 2,3,3,3-tetrafluoropropene

Water (380 gm/hour) is passed through steam jacketed preheater, where the temperature is raised to 160° C. followed by electrical super heater where the temperature of steam is raised to 800° C. This superheated steam goes to the reactor whose temperature is maintained at 775° C. either by superheated steam or by electrical heaters. After adjusting the water flow rate, R-22 and R-40 are passed through their respective preheaters at the rate of 139 gm/hr and 245 gm/hr respectively and then mixed in organic super heater where the temperature is maintained at 600° C. followed by reactor which is maintained at 775° C. The residence time in the reaction system is maintained at around 0.5 seconds. The analysis of Reactor 1 outlet is given below after eliminating water and acids.

| | | | |
|---|---|---|---|
| Methane | 0.34% | HFP | 0.16% |
| TFE | 6.79% | R22 | 2.19% |
| R23 | 0.13% | R-1234yf | 3.67% |
| VdF | 6.28% | OFCB | 0.13% |
| Trifluoroethene | 0.06% | C-1 | 77.47% |
| R-32 | 0.23% | R-134 | 0.20% |
| CTFE | 0.15% | R-124 | 0.06% |

This stream was made acid free and anhydrous by passing these stream through quencher, caustic scrubber, sulphuric scrubber and alumina balls. This anhydrous stream was distilled and then passed through 4 Å molecular sieves bed to obtain a mixture of composition given below:

| | | | |
|---|---|---|---|
| Methane: 2.15%; | | TFE: 43.03% | |
| VdF: 39.92% | | R-23: 0.82% | |
| TriFEthene: 0.38% | | R-22: 13.88% | |
| HFP: 1.01% | | | |

In this stream, $CH_2$ group of R-1234yf comes from methane and VdF while $CF_2$ group of R-1234yf comes from TFE, VdF, R-23, R-22 and HFP. This stream was passed to second reactor to obtain the following composition:

| | | | |
|---|---|---|---|
| Methane: 0.54% | | TFE: 37.68% | |
| VdF: 29.52% | | CTFE: 0.0027% | |
| R-22: 0.176% | | R-1234yf: 24.09% | |

Example 8: Process for the Preparation of 2,3,3,3-tetrafluoropropene

A mixture of chlorodifluoromethane and methyl chloride in the mole ratio of 1:3.55 respectively is preheated and the then superheated till 400° C. and then mixed with 800° C. steam (50% by weight of total feed) in the reactor. The reactor temperature is maintained at 793° C. by electrical furnace. The residence time in the reactor is kept around 0.5 seconds. The reactor outlet compositions in mol % after removing steam and acids are as follows:

The analysis of reactor outlet is given below after eliminating water and acids.

| | | | |
|---|---|---|---|
| Methane | 0.61% | Chlorodifluoromethane | 1.43% |
| Tetrafluoroethyelene | 3.39% | 2,3,3,3-Tetrafluoropropene | 3.51% |
| Trifluoromethane | 0.11% | Octafluorocyclobutane | 0.08% |
| Vinylidene fluoride | 9.91% | Methyl chloride | 78.98% |
| Trifluoroethene | 0.05% | Tetrafluoroethane | 0.35% |
| Difluoromethane | 0.26% | Chlorotetrafluoroethane | 0.02% |
| Chlorotrifluoroethene | 0.10% | (R-124a) | |
| Hexafluoropropene | 0.20% | Chlorotetrafluoroethane (R-124) | 0.04% |
| | | Heavies | 0.917% |

Purification with Methanol

For checking the effect of solvent scrubbing, the reactor was operated at 750° C. and the molar ratio of water:R-22: methyl chloride was maintained at 80%:10%:10% with a residence time of 0.5 seconds. The reactor feed consists of 403 g/hour of Steam, 242 g/hour of R-22 and 141 g/hour of methyl chloride. The reactor outlet stream was passed through water scrubber to remove the acids and then passed through drying agent. The methanol scrubber consists of a 4 liters. Jacketed Vessel over which 3 m packed height column was placed. 2.5 kg of methanol was taken in a scrubber and circulated from 1.5 m packed height at the rate of 7LPH. The temperature of the jacketed vessel was maintained between −15° C. to −20° C. by passing chilled brine in the jacket. The reactor outlet stream free of acids is passed near the bottom of the packed column. The analysis results before and after passing through methanol scrubber is given below.

| | Before Methanol Scrubber | After Methanol Scrubber Time of scrubbing | |
|---|---|---|---|
| | | 40 minutes | 90 minutes |
| Methane | 2.3668% | 1.9106% | 3.8551% | 2.5168% |
| Tetrafluoroethyelene | 26.9654% | 26.6275% | 71.1367% | 59.5873% |

|  | Before Methanol Scrubber | After Methanol Scrubber Time of scrubbing | |
|---|---|---|---|
|  |  | 40 minutes | 90 minutes |
| Trifluoromethane | 0.3413% | 0.3255% | 0.5120% | 0.5678% |
| Vinylidene fluoride | 3.0579% | 2.9936% | 6.3302% | 5.9810% |
| Trifluoroethene | 0.1308% | 0.1136% | 0.1169% | 0.1921% |
| Difluoromethane | 0.4932% | 0.4545% | 0.3822% | 0.4986% |
| Chlorotrifluoroethene | 0.1513% | 0.1711% | 0.3255% | 0.3335% |
| Hexafluoropropene | 0.1335% | 0.1319% | 0.1561% | 0.2109% |
| Chlorodifluoromethane | 10.3373% | 9.8081% | 2.6778% | 5.0420% |
| 2,3,3,3-etrafluoropropene | 1.9401% | 1.9312% | 2.3089% | 3.0510% |
| Octafluorocyclobutane | 0.2621% | 0.2007% | 0.0625% | 0.2085% |
| Methyl chloride | 53.2398% | 54.8120% | 12.0373% | 21.6338% |
| Chlorotetrafluoroethane (R-124a) | 0.0763% | 0.0333% | 0.0000% | 0.0000% |
| Chlorotetrafluoroethane (R-124) | 0.0536% | 0.0452% | 0.0000% | 0.0000% |

Purification with Trichloroethyelene

The procedure followed is same as given in example 1, here the solvent has been changed to trichloroethyelene. 4 kgs of Trichloroethyelene was taken for scrubbing. The analysis results before and after passing through trichloroethyelene is given below.

|  | Before TCE Scrubber | After TCE Scrubber | | |
|---|---|---|---|---|
| Methane | 0.5492% | 1.0334% | 0.6427% | 0.5312% |
| Tetrafluoroethyelene | 21.0258% | 58.1862% | 47.0447% | 38.4720% |
| Trifluoromethane | 0.1854% | 0.2654% | 0.4253% | 0.3509% |
| Vinylidene fluoride | 1.6590% | 7.1405% | 6.2605% | 5.6319% |
| Trifluoroethene | 0.0484% | 0.1138% | 0.1317% | 0.1175% |
| Difluoromethane | 0.1686% | 0.2625% | 0.3377% | 0.2960% |
| Chlorotrifluoroethene | 0.1098% | 0.2380% | 0.3149% | 0.2940% |
| Hexafluoropropene | 0.1046% | 0.0528% | 0.1390% | 0.1658% |
| Chlorodifluoromethane | 27.7009% | 10.4771% | 14.8363% | 16.0611% |
| 2,3,3,3-tetrafluoropropene | 1.1494% | 2.7354% | 3.2141% | 3.5169% |
| Octafluorocyclobutane | 0.1037% | 0.1922% | 0.1860% | 0.2095% |
| Methyl chloride | 46.7794% | 13.3714% | 21.3325% | 29.4327% |
| Chlorotetrafluoroethane (R-124a) | 0.0539% | 0.0385% | 0.0240% | 0.0398% |
| Chlorotetrafluoroethane (R-124) | 0.0713% | 0.0000% | 0.0606% | 0.0773% |

Purification with Chloroform

The procedure followed is same as given in example 1, here the solvent has been changed to chloroform. 4 kg of chloroform was taken for scrubbing. The analysis results before and after passing through chloroform is given below.

|  | Before C3 Scrubber | After C3 Scrubber | | |
|---|---|---|---|---|
| Methane | 0.1922% | 0.6033% | 0.4514% | 0.2954% |
| Tetrafluoroethyelene | 23.9417% | 48.3656% | 56.7726% | 38.7284% |
| Trifluoromethane | 0.1010% | 0.3540% | 0.5103% | 0.4225% |
| Vinylidene fluoride | 1.1235% | 3.1519% | 7.4865% | 8.0002% |
| Trifluoroethene | 0.0370% | 0.0672% | 0.1116% | 0.1171% |
| Difluoromethane | 0.0446% | 0.0336% | 0.1614% | 0.2117% |
| Chlorotrifluoroethene | 0.0966% | 0.1487% | 0.4312% | 0.4439% |
| Hexafluoropropene | 0.0454% | 0.0000% | 0.0000% | 0.1581% |
| Chlorodifluoromethane | 29.8098% | 0.1139% | 4.0906% | 16.6569% |
| 2,3,3,3-Tetrafluoropropene | 0.8911% | 0.3750% | 2.1269% | 4.7536% |
| Octafluorocyclobutane | 0.0465% | 0.0000% | 0.0609% | 0.1661% |
| Methyl chloride | 42.0800% | 0.1579% | 3.4045% | 10.8744% |
| Chlorotetrafluoroethane (R-124a) | 0.0356% | 0.0000% | 0.0000% | 0.0438% |
| Chlorotetrafluoroethane (R-124) | 0.0375% | 0.0000% | 0.0000% | 0.0467% |

The analysis result of solvent chloroform after scrubbing is given below:

| Hexafluoropropene | 0.008% |
|---|---|
| Octafluorocyclobutane | 0.008% |
| 2,3,3,3-Tetrafluoropropene | 0.240% |
| chlorodifluoromethane | 0.147% |
| Methyl chloride | 19.163% |
| Chloroform | 80.431% |

Purification with Methylene Chloride

The procedure followed is same as given in example 1, here the solvent has been changed to methylene chloride. 4 kg of methylene chloride was taken for scrubbing. The analysis results before and after passing through methylene chloride is given below.

|  | Before C2 Scrubber | After C2 Scrubber | |
|---|---|---|---|
| Methane | 0.1638% | 0.3703% | 0.1404% |
| Tetrafluoroethyelene | 22.3233% | 40.7030% | 21.2515% |
| Trifluoromethane | 0.2112% | 0.3343% | 0.1751% |
| Vinylidene fluoride | 5.2918% | 5.9353% | 4.9834% |
| Trifluoroethene | 0.0709% | 0.0129% | 0.0642% |
| Difluoromethane | 0.1436% | 0.0000% | 0.1287% |
| Chlorotrifluoroethene | 0.2417% | 0.2393% | 0.2284% |
| Hexafluoropropene | 0.2101% | 0.0000% | 0.2020% |
| Chlorodifluoromethane | 5.5228% | 0.0319% | 5.1449% |
| 2,3,3,3-Tetrafluoropropene | 3.6240% | 0.4812% | 3.5295% |
| Octafluorocyclobutane | 0.1130% | 0.0000% | 0.1186% |
| Methyl chloride | 61.3566% | 0.1915% | 34.3825% |
| Chlorotetrafluoroethane (R-124a) | 0.0249% | 0.0000% | 0.0261% |
| Chlorotetrafluoroethane (R-124) | 0.1056% | 0.0000% | 0.0842% |

The analysis result of solvent methylene chloride after scrubbing is

| Hexafluoropropene | 0.007% |
|---|---|
| Octafluorocyclobutane | 0.015% |
| 2,3,3,3-Tetrafluoropropene | 0.078% |
| Chlorodifluoromethane | 0.066% |
| Methyl chloride | 13.310% |
| Methyelene chloride | 85.780% |

ABBREVIATION USED IN THE EXAMPLES

Tetrafluoroethyelene: TFE
Trifluoromethane: R-23
Vinylidenefluoride: VdF
1,1,2-Trifluoroethene: TriFEthene
Difluoromethane: R-32
Chlorotrifluoroethylene: CTFE
Hexafluoropropene: HFP
Chlorodifluoromethane: R-22

2,3,3,3-Tetrafluoropropene: R-1234yf
Octafluorocyclobutane: OFCB
Methyl chloride: C-1
1-Chloro-1,2,2,2-Tetrafluoroethane: R-124
1-Chloro-1,1,2,2-Tetrafluoroethane: R-124a

We claim:

1. A process for preparation of 2,3,3,3-tetrafluoropropene comprising:
    a) providing a mixture of methyl chloride and chlorodifluoromethane, said mixture is either premixed or added separately;
    b) providing and contacting heat medium with step a) mixture to form second mixture comprising 2,3,3,3-tetrafluoropropene, methyl chloride and fluorinated compounds having boiling point in the range of 14 to 90° C.;
    c) drying the second mixture of step b) to obtain anhydrous second mixture;
    d) subjecting the anhydrous second mixture of step c) to distillation to obtain anhydrous third mixture comprising methane, trifluoromethane, chlorotrifluoroethene, chlorodifluoromethane, tetrafluoroethyelene, vinylidene fluoride and difluoromethane and anhydrous fourth mixture comprising 2,3,3,3-tetrafluoropropene, methyl chloride, octafluorocyclobutane, chlorotrifluoroethyelene and tetrafluorochloroethane;
    e) contacting the anhydrous third mixture of step d) with molecular sieve of size 3 Å to 5 Å to obtain a fifth mixture, said mixture is free of difluoromethane and is recycled;
    f) subjecting the anhydrous fourth mixture of step d) to distillation to obtain anhydrous sixth mixture comprising 2,3,3,3-tetrafluoropropene and methyl chloride;
    g) optionally, purifying the anhydrous sixth mixture by contacting with solvent in a solvent scrubber;
    h) contacting the anhydrous sixth mixture of step f) or step g) with molecular sieve of size 3 Å to 5 Å to obtain seventh mixture, said mixture is free of methyl chloride; and
    i) isolating 2,3,3,3-tetrafluoropropene from the seventh mixture of step h).

2. The process of claim 1, wherein the reactor is heated at a temperature in range of 550° C. to 900° C. or providing a steam medium to the mixture of methyl chloride and chlorodifluoromethane to obtain the temperature range of 550° C. to 900° C. or both to obtain the step b) second mixture.

3. The process of claim 1, wherein the step c) anhydrous second mixture is obtained by passing the second mixture through water quencher, caustic scrubber, sulphuric scrubber, alumina balls or calcium chloride.

4. The process of claim 1, wherein step e) or step h) further comprises regenerating the molecular sieves and recovering the adsorbed material.

5. A process for preparation of 2,3,3,3-tetrafluoropropene comprising:
    a) providing a mixture of methyl chloride to chlorodifluoromethane in first reactor, wherein said mixture is either premixed or added separately;
    b) providing and contacting the heat medium with step a) mixture to form second mixture comprising 2,3,3,3-tetrafluoropropene, methyl chloride and the fluorinated compounds having a boiling point in the range of −14 to −90° C.;
    c) drying second mixture of step b) to obtain anhydrous second mixture;
    d) subjecting the anhydrous second mixture of step c) to distillation to obtain anhydrous third mixture comprising methane, trifluoromethane, chlorotrifluoroethene, chlorodifluoromethane, tetrafluoroethyelene, vinylidene fluoride and difluoromethane and anhydrous fourth mixture comprising 2,3,3,3-tetrafluoropropene, methyl chloride, octafluorocyclobutane, chlorotrifluoroethyelene and tetrafluorochloroethane;
    e) contacting the anhydrous third mixture of step d) with molecular sieve of size 3 Å to 5 Å to obtain a fifth mixture, said mixture is free of difluoromethane;
    f) providing the fifth mixture and steam into a second reactor to obtain a second mixture;
    g) drying the second mixture to obtain anhydrous second mixture, alone or in combination with step c);
    h) subjecting the anhydrous second mixture of step g) to distillation to obtain anhydrous third mixture comprising methane, tetrafluoroethyelene, vinylidene fluoride and difluoromethane and anhydrous fourth mixture comprising 2,3,3,3-tetrafluoropropene, methyl chloride, octafluorocyclobutane, chlorotrifluoroethyelene and tetrafluorochloroethane, alone or in combination with step d);
    i) subjecting the anhydrous fourth mixture of step d) and/or step h) to distillation to obtain anhydrous sixth mixture comprising 2,3,3,3-tetrafluoropropene and methyl chloride, and another mixture comprising methyl chloride, octafluorocyclobutane, chlorotetrafluoroethane and tetrafluoroethane;
    j) contacting the anhydrous sixth mixture of step i) with molecular sieve of size 3 Å to 5 Å to obtain seventh mixture, said mixture is free of methyl chloride; and
    k) isolating 2,3,3,3-tetrafluoropropene from seventh mixture of step j).

6. A process for preparation of 2,3,3,3-tetrafluoropropene comprising:
    a) providing a mixture of methyl chloride to chlorodifluoromethane in a first reactor, said mixture is either premixed or added separately;
    b) providing and contacting heat medium with step a) mixture to form a second mixture comprising 2,3,3,3-tetrafluoropropene, methyl chloride and fluorinated compounds having a boiling point in the range of −14 to −90° C.;
    c) drying the second mixture of step b) to obtain an anhydrous second mixture;
    d) contacting the anhydrous second mixture of step c) with a solvent to obtain an anhydrous mixture 3' in gas phase and anhydrous mixture 4' in liquid phase, wherein the anhydrous mixture 3' comprises methane, tetrafluoroethyelene, trifluoromethane, vinylidene fluoride, difluoromethane, chlorotrifluoroethene, hexafluoropropene, chlorodifluoromethane, 2,3,3,3-tetrafluoropropene, octafluorocyclobutane and methyl chloride and anhydrous mixture 4' comprises solvent and methyl chloride;
    e) contacting the anhydrous mixture 3' with 4 Å molecular sieves to obtain a mixture 5', wherein the mixture 5' is free of methyl chloride and difluoromethane;
    f) subjecting the anhydrous mixture 4' of step d) to distillation to obtain a mixture 7' comprising methyl chloride which is recycled into the existing reactor and mixture 8' comprising solvent which is reused;
    g) subjecting the mixture 5' of step e) to distillation to obtain a mixture 9' comprising methane, tetrafluoroethyelene, trifluoromethane, vinylidene fluoride, hexafluoropropene and chlorodifluoromethane and a mixture 10' comprising chlorotrifluoroethyelene, 2,3,3, 3-tetrafluoropropene, octafluorocyclobutane, tetrafluorochloroethane and tetrafluoroethane;

h) recycling mixture 9' of step g) to the existing reactor or to the second reactor;

i) subjecting the mixture 10' of step g) to distillation to obtain a mixture 11' comprising 2,3,3,3-tetrafluoropropene and chlorotrifluoroethyelene and a mixture 12' comprising octafluorocyclobutane, chlorotetrafluoroethanes, tetrafluoroethane and heavies;

j) subjecting the mixture 12' of step i) to distillation to obtain a mixture 13' comprising octafluorocyclobutane, chlorotetrafluoroethanes and tetrafluoroethanes which is recycled into reactor, and k) isolating 2,3,3,3-tetrafluoropropene from the mixture 11'.

7. The process of claim 6, wherein the solvent comprises chloroform, dichloromethane, trichloroethylene, methanol or a mixture thereof.

\* \* \* \* \*